United States Patent [19]

Ertl

[11] Patent Number: 4,771,091
[45] Date of Patent: Sep. 13, 1988

[54] SUBSTITUTED DIAZAOXASPIRODECANES, PREPARATION THEREOF AND USE THEREOF AS STABILIZERS FOR POLYMERS

[75] Inventor: Josef Ertl, Wertingen, Fed. Rep. of Germany

[73] Assignee: Hoechst Aktiengesellschaft, Frankfurt, Fed. Rep. of Germany

[21] Appl. No.: 934,019

[22] Filed: Nov. 24, 1986

[30] Foreign Application Priority Data

Nov. 26, 1985 [DE]  Fed. Rep. of Germany ....... 3541665

[51] Int. Cl.$^4$ .................. C08K 5/35; C08G 65/08; C07D 491/10
[52] U.S. Cl. ........................... 524/97; 524/96; 546/16; 546/18; 546/19; 546/20; 528/87; 528/211
[58] Field of Search .............. 546/18, 19, 20, 16; 524/96, 97

[56] References Cited

U.S. PATENT DOCUMENTS

| | | | |
|---|---|---|---|
| 4,319,030 | 3/1982 | Wiezer et al. | 546/20 |
| 4,340,534 | 7/1982 | Wiezer et al. | 524/102 |
| 4,405,735 | 9/1983 | Wiezer et al. | 524/95 |

FOREIGN PATENT DOCUMENTS

| | | |
|---|---|---|
| 2606026 | 8/1977 | Fed. Rep. of Germany . |
| 2941004 | 4/1981 | Fed. Rep. of Germany ........ 546/19 |
| 3104294 | 8/1982 | Fed. Rep. of Germany . |
| 1582525 | 10/1969 | France .................................. 546/20 |

Primary Examiner—Kriellion Morgan
Attorney, Agent, or Firm—Connolly and Hutz

[57] ABSTRACT

Novel diazaspirodecanes of the general formula

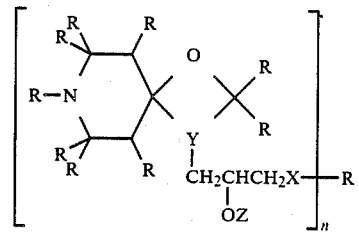

are prepared from known diazaspirodecane compounds and epoxy compounds or by reacting diazaspirodecane-substituted epoxy compounds with alcohols or amines and are excellent light stabilizers for synthetic polymers.

12 Claims, No Drawings

SUBSTITUTED DIAZAOXASPIRODECANES, PREPARATION THEREOF AND USE THEREOF AS STABILIZERS FOR POLYMERS

The present invention relates to novel sterically hindered amine light stabilizers which protect synthetic polymers from the action of light, heat and oxygen.

German Offenlegungsschrift No. 3,104,294 encompasses inter alia polyalkylpiperidine light stabilizers of the formula

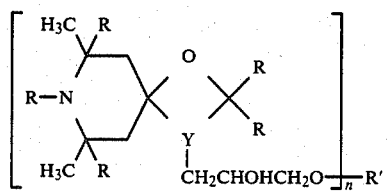

where n stands for 1 to 3 and

R' when n=1 stands for hydrogen, phenyl, for $C_1$- to $C_{30}$-alkyl, for a $C_1$- to $C_{18}$-alkyl-substituted, $C_5$- to $C_6$-cycloalkyl-substituted or phenyl-substituted acyl or carbamoyl group whose

group is bonded to the oxygen,

R' when n=2 stands for $C_2$- to $C_{18}$-alkylene, for phenylene which is unsubstituted or substituted by up to two $C_1$- to $C_4$-alkyl groups, for $\alpha,\omega$-dicarboxy-$C_1$- to $C_8$-alkylene, for a dicarboxy-$C_6$-ring, for $C_7$- to $C_{14}$-aralkylene R' when n=3 stands for an isocyanuric acid radical or a —CH$_2$CH—CH$_2$— radical.

The present invention, then, relates to compounds of the formula (I)

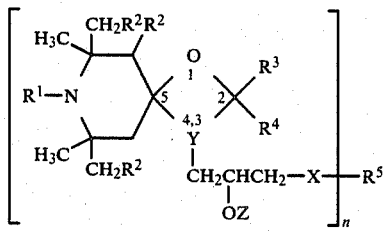

in which n is equal to 1 to 20, preferably 2 to 10, in particular 2 to 5, $R^1$ is hydrogen, $C_1$- to $C_4$-alkyl, benzyl, allyl, $C_2$- to $C_{30}$-alkanoyl, $C_3$- to $C_{20}$-alkenoyl, $C_7$- to $C_{11}$-aroyl, $C_8$- to $C_{14}$-arylalkanoyl or $C_8$- to $C_{20}$-alkylaryl, preferably hydrogen, $C_1$- to $C_4$-alkyl, $C_2$- to $C_{30}$-alkanoyl, in particular hydrogen or acyl, very particularly preferably hydrogen, $R^2$ is hydrogen or $C_1$- to $C_4$-alkyl, preferably hydrogen, $R^3$ and $R^4$ are identical or different and denote hydrogen, $C_1$- to $C_{18}$-alkyl, preferably $C_1$- to $C_{13}$- and in particular $C_1$- to $C_9$-alkyl, unsubstituted or chlorine- or $C_1$- to $C_4$-alkyl-substituted phenyl, unsubstituted or $C_1$- to $C_4$-alkyl-substituted $C_7$- to $C_{14}$-aralkyl, preferably $C_7$- to $C_9$-phenylalkyl, or together with the carbon atom connecting these radicals denote a $C_5$- to $C_{12}$-cycloalkyl or piperidine ring which is unsubstituted or substituted by up to four $C_1$- to $C_4$-alkyl groups, $R^5$ when n=1 denotes a piperidine ring which is substituted by 1 to 4 $C_1$- to $C_4$-alkyl groups, preferably 2,2,6,6-tetramethyl-4-piperidinyl, $R^5$ when n=2 denotes cycloalkylene, dicycloalkylene, tricycloalkylene, bismethylenemonocycloalkylene, bismethylenedicycloalkylene, bis-methylenetricycloalkylene, arylene, bis-arylenealkyl, which radicals can also be bromine- or chlorine- or $C_1$- to $C_4$-alkyl-substituted, a radical

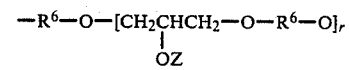

with r=1 to 20 and $R^6$ is equal to $C_2$- to $C_{12}$-alkylene, cycloalkylene, dicycloalkylene, tricycloalkylene, bismethylenemonocycloalkylene, bismethylenedicycloalkylene, bismethylenetricycloalkylene, arylene, bisarylenealkyl, which radicals can also be bromine- or chlorine- or $C_1$- to $C_4$-alkyl-substituted, $R^5$ when n=3 denotes the radical of a trifunctional alcohol or amine, preferably the glycerol radical, the trifunctional radical of an aliphatic alcohol which contains further hydroxyl groups, preferably

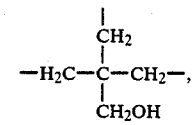

the trifunctional radical of a novolak based on phenol, cresol, bisphenol-F or bisphenol-A, $R^5$ when n=4 denotes the tetrafunctional radical of an aliphatic alcohol or amine, preferably the pentaerythrityl radical, or of a novolak based on phenol, cresol, bisphenol-F or bisphenol-A or the radial

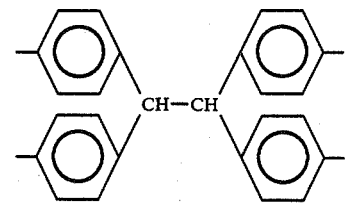

$R^5$ when n>4 denotes a polyfunctional radical of a polyol, of a polyamine, of a novolak based on phenol, cresol, bisphenol-F or bisphenol-A, Y denotes

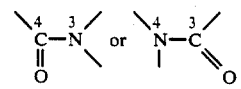

and occupies ring positions 3, 4 in the formula (I),

X represents

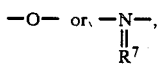 —O— or —N—,
$\overset{\|}{R^7}$ where $R^7$ is hydrogen, $C_1$- to $C_{30}$-alkyl, a piperidine ring which is substituted by 1 to 4 $C_1$- to $C_4$-alkyl groups, or a radical of the formula (II)

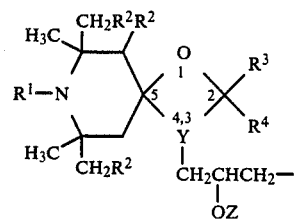
(II)

in which $R^1$, $R^2$, $R^3$, $R^4$ and Y have the above-mentioned meanings,

Z is hydrogen or $R^5$ denotes in addition to the abovementioned meanings when n=1 hydrogen, $C_1$- to $C_{30}$-alkyl, aryl, aralkyl, alkylaryl or a piperidine ring which is substituted by 1 to 4 $C_1$- to $C_4$-alkyl groups and when n=2 $C_2$- to $C_{18}$-alkylene or phenylene, in which case X must then be equal to

In addition the grouping

from the formula (I) stands
when n=2 for

and
when n>2 for a polyamine of the formulae

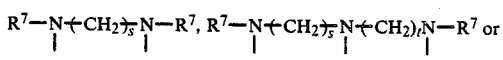

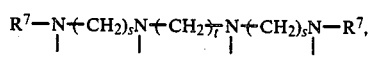

where $R^7$ has the abovementioned meaning and s and t are whole numbers from 2 to 4.

The novel compounds of the formula I are prepared from diazaspirodecanes of the formula (IVa) or (IVb)

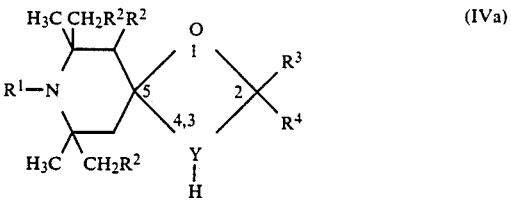
(IVa)

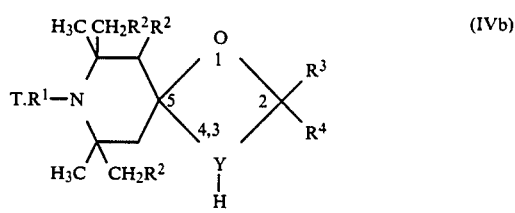
(IVb)

in which $R^1$, $R^2$, $R^3$, $R^4$ and Y have the abovementioned meanings and T is a nonoxidizing mineral acid or an aliphatic or aromatic sulfonic or phosphonic acid, an aliphatic mono-, di- or poly-carboxylic acid or an aromatic mono- or di-carboxylic acid, and (A) epoxides of the formula (Va) or (Vb)

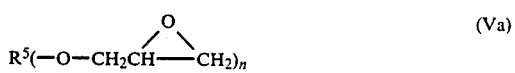
(Va)

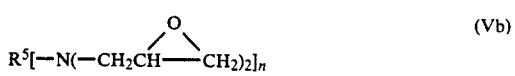
(Vb)

in which $R^5$ and n have the abovementioned meanings, in an inert solvent in the presence of a base and if desired of a phase transfer catalyst at 40° to 180° C., or (B) the compounds of the formula (IV) are reacted with epichlorohydrin to give a compound of the formula (VI)

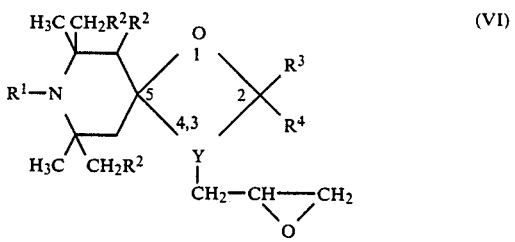
(VI)

and this compound of the formula (VI) is then reacted with an alcohol of the formula (VII)

(VII)

or an amine of the formula (VIII)

(VIII)

in which $R^1$, $R^2$, $R^3$, $R^4$, $R^5$, $R^7$, Y and n have the abovementioned meanings, or a polyamine of the formula (IX)

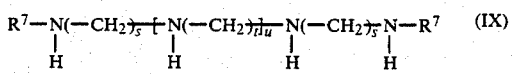

in which $R^7$, s and t have the abovementioned meanings and u is a whole number from 0 to 3.

In the case of reaction pathway A and also in the case of the reaction of compounds of the formula (IV) with epichlorohydrin (pathway B, part 1), an inert organic solvent, such as, for example toluene or xylene, is used. The reaction is carried out in the presence of 0.2 to 1.5 times the equivalent amount of a base, relative to the compound IVa, or 1.2 to 2.5 times the equivalent amount of a base in the case of using a compound IVb, preferably with 0.3 to 1.2 times or 1.3 to 2.2 times the equivalent amount of sodium hydroxide or potassium hydroxide. If desired, phase transfer catalysts are added. The compounds IV are used in the reaction in 0.9 to 1.1 times the equivalent amount, preferably in 0.95 to 1.05 times the equivalent amount, particularly preferably in the equivalence ratio of 1:1, based on the epoxy groups in the compounds V. The reaction is effected at 40°–180° C., preferably at 50°–150° C., particularly preferably at 80°–110° C.

The reaction of the 1-diazaspirodecane-substituted 2,3-epoxypropyl compound VI in pathway B with alcohols or amines is effected by methods known in principle.

The starting materials of the formula (IVa) or (IVb) are already good stabilizers themselves, but are not entirely satisfactory in particular in respect of the compatibility with the polymer to be stabilized and in respect of volatility. The stabilizers according to the invention do not have these disadvantages and surprisingly also have a distinctly better antioxidative and light-stabilizing action.

Compared with the compounds of German Offenlegungsschrift No. 3,104,294, the novel stabilizers have better properties, in particular a better antioxidative action and distinctly better light-stabilizing action, which could not be expected.

Suitable compounds of the formula (IVa) are for example:
1. 2-Butyl-7,7,9,9,-tetramethyl-1-oxa-3,8-diaza-4-oxo-spiro-[4.5]-decane
2. 2-iso-Butyl-7,7,9,9,-tetramethyl-1-oxa-3,8-diaza-4-oxo-spiro-[4.5]-decane
3. 2-Pentyl-7,7,9,9,-tetramethyl-1-oxa-3,8-diaza-4-oxo-spiro-[4.5]-decane
4. 2-iso-Pentyl-7,7,9,9,-tetramethyl-1-oxa-3,8-diaza-4-oxa-spiro-[4.5]-decane
5. 2-Hexyl-7,7,9,9,-tetramethyl-1-oxa-3,8-diaza-4-oxo-spiro-[4.5]-decane
6. 2-Heptyl-7,7,9,9,-tetramethyl-1-oxa-3,8-diaza-4-oxo-spiro-[4.5]-decane
7. 2-iso-Heptyl-7,7,9,9,-tetramethyl-1-oxa-3,8-diaza-4-oxo-spiro-[4.5]-decane
8. 2-Nonyl-7,7,9,9,-tetramethyl-1-oxa-3,8-diaza-4-oxo-spiro-[4.5]-decane
9. 2-iso-Nonyl-7,7,9,9,-tetramethyl-1-oxa-3,8-diaza-4-oxo-spiro-[4.5]-decane
10. 2-Undecyl-7,7,9,9,-tetramethyl-1-oxa-3,8-diaza-4-oxo-spiro-[4.5]-decane
11. 2-Phenyl-7,7,9,9,-tetramethyl-1-oxa-3,8-diaza-4-oxo-spiro-[4.5]-decane
12. 2-(4-Chloro-phenyl)-7,7,9,9,-tetramethyl-1-oxa-3,8-diaza-4-oxo-spiro-[4.5]-decane
13. 2-Ethyl-2,7,7,9,9,-pentamethyl-1-oxa-3,8-diaza-4-oxo-spiro-[4.5]-decane
14. 2-Propyl-2,7,7,9,9,-pentamethyl-1-oxa-3,8-diaza-4-oxo-spiro-[4.5]-decane
15. 2-iso-Propyl-2,7,7,9,9,-pentamethyl-1-oxa-3,8-diaza-4-oxo-spiro-[4.5]-decane
16. 2-Butyl-2,7,7,9,9,-pentamethyl-1-oxa-3,8-diaza-4-oxo-spiro-[4.5]-decane
17. 2-iso-Butyl-2,7,7,9,9,-pentamethyl-1-oxa-3,8-diaza-4-oxo-spiro-[4.5]-decane
18. 2-Pentyl-2,7,7,9,9,-pentamethyl-1-oxa-3,8-diaza-4-oxo-spiro-[4.5]-decane
19. 2-Hexyl-2,7,7,9,9,-pentamethyl-1-oxa-3,8-diaza-4-oxo-spiro-[4.5]-decane
20. 2-Nonyl-2,7,7,9,9,-pentamethyl-1-oxa-3,8-diaza-4-oxo-spiro-[4.5]-decane
21. 2,2,7,7,9,9-Hexamethyl-1-oxa-3,8-diaza-4-oxo-spiro-[4.5]-decane
22. 2,2,7,7,8,9,9-Heptamethyl-1-oxa-3,8-diaza-4-oxo-spiro-[4.5]-decane
23. 2,2-Diethyl-7,7,9,9,-tetramethyl-1-oxa-3,8-diaza-4-oxo-spiro-[4.5]decane
24. 2,2-Dipropyl-7,7,9,9,-tetramethyl-1-oxa-3,8-diaza-4-oxo-spiro-[4.5]-decane
25. 2,2-Dibutyl-7,7,9,9,-tetramethyl-1-oxa-3,8-diaza-4-oxo-spiro-[4.5]-decane
26. 2-Ethyl-2-pentyl-7,7,9,9,-tetramethyl-1-oxa-3,8-diaza-4-oxo-spiro-[4.5]-decane
27. 2,2-Dibenzyl-7,7,9,9,-tetramethyl-1-oxa-3,8-diaza-4-oxo-spiro-[4.5]-decane
28. 2,2,4,4-Tetramethyl-7-oxa-3,13-diaza-14-oxo-dispiro-[5.1.4.2]-tetradecane
29. 2,2,4,4-Tetramethyl-7-oxa-3,14-diaza-15-oxo-dispiro-[5.1.5.2]-pentadecane
30. 2,2,4,4-Tetramethyl-7-oxa-3,20-diaza-21-oxo-dispiro-[5.1.11.2]-heneicosane
31. 2,2,7,7,9,9-Hexamethyl-1-oxa-3,8-diaza-4-oxo-8-acetyl-spiro-[4.5]-decane
32. 2,2,4,4-Tetramethyl-7-oxa-3,14-diaza-15-oxo-3-acetyl-dispiro-[5.1.5.2]-pentadecane
33. 2,2,4,4-Tetramethyl-7-oxa-3,20-diaza-21-oxo-3-acetyl-dispiro-[5.1.11.2]-heneicosane
34. 2,7,7,9,9-Pentamethyl-1-oxa-4,8-diaza-3-oxo-spiro-[4.5]-decane
35. 2-Ethyl-7,7,9,9-tetramethyl-1-oxa-4,8-diaza-3-oxo-spiro-[4.5]-decane
36. 2-Propyl-7,7,9,9-tetramethyl-1-oxa-4,8-diaza-3-oxo-spiro-[4.5]-decane
37. 2-Butyl-7,7,9,9-tetramethyl-1-oxa-4,8-diaza-3-oxo-spiro-[4.5]-decane
38. 2-iso-Butyl-7,7,9,9-tetramethyl-1-oxa-4,8-diaza-3-oxa-spiro-[4.5]-decane
39. 2-Pentyl-7,7,9,9-tetramethyl-1-oxa-4,8-diaza-3-oxo-spiro-[4.5]-decane
40. 2-iso-Pentyl-7,7,9,9-tetramethyl-1-oxa-4,8-diaza-3-oxo-spiro-[4.5]-decane
41. 2-iso-Heptyl-7,7,9,9-tetramethyl-1-oxa-4,8-diaza-3-oxo-spiro-[4.5]-decane
42. 2-Phenyl-7,7,9,9-tetramethyl-1-oxa-4,8-diaza-3-oxo-spiro-[4.5]-decane
43. 2,2,7,7,9,9-Hexamethyl-1-oxa-4,8-diaza-3-oxo-spiro-[4.5]-decane
44. 2,2,7,7,8,9,9-Heptamethyl-1-oxa-4,8-diaza-3-oxo-spiro-[4.5]-decane
45. 2,2-Diethyl-7,7,9,9-tetramethyl-1-oxa-4,8-diaza-3-oxo-spiro-[4.5]-decane
46. 2,2-Diethyl-7,7,8,9,9-pentamethyl-1-oxa-4,8-diaza-3-oxo-spiro-[4.5]-decane 47. 2,2-Dipropyl-7,7,9,9-tetramethyl-1-oxa-4,8-diaza-3-oxo-spiro-[4.5]-decane
48. 2,2-Dibutyl-7,7,9,9-tetramethyl-1-oxa-4,8-diaza-3-oxo-spiro-[4.5]-decane
49. 2,2-Dipentyl-7,7,9,9-tetramethyl-1-oxa-4,8-diaza-3-oxo-spiro-[4.5]-decane
50. 2-Ethyl-2,7,7,9,9-pentamethyl-1-oxa-4,8-diaza-3-oxo-spiro-[4.5]-decane
51. 2-Propyl-2,7,7,9,9-pentamethyl-1-oxa-4,8-diaza-3-oxo-spiro-[4.5]-decane
52. 2-iso-Propyl-2,7,7,9,9-pentamethyl-1-oxa-4,8-diaza-3-oxo-spiro-[4.5]-decane
53. 2-Butyl-2,7,7,9,9-pentamethyl-1-oxa-4,8-diaza-3-oxo-spiro-[4.5]-decane
54. 2-iso-Butyl-2,7,7,9,9-pentamethyl-1-oxa-4,8-diaza-3-oxo-spiro-[4.5]-decane
55. 2-Pentyl-2,7,7,9,9-pentamethyl-1-oxa-4,8-diaza-3-oxo-spiro-[4.5]decane
56. 2-iso-Pentyl-2,7,7,9,9-pentamethyl-1-oxa-4,8-diaza-3-oxo-spiro-[4.5]-decane
57. 2-Hexyl-2,7,7,9,9-pentamethyl-1-oxa-4,8-diaza-3-oxo-spiro-[4.5]-decane
58. 2-Heptyl-2,7,7,9,9-pentamethyl-1-oxa-4,8-diaza-3-oxo-spiro-[4.5]-decane
59. 2-Nonyl-2,7,7,9,9-pentamethyl-1-oxa-4,8-diaza-3-oxo-spiro-[4.5]-decane
60. 2-Undecyl-2,7,7,9,9-pentamethyl-1-oxa-4,8-diaza-3-oxo-spiro-[4.5]-decane
61. 2-Ethyl-2-butyl-7,7,9,9-tetramethyl-1-oxa-4,8-diaza-3-oxo-spiro-[4.5]-decane
62. 2-Ethyl-2-pentyl-7,7,9,9-tetramethyl-1-oxa-4,8-diaza-3-oxo-spiro-[4.5]-decane
63. 2-Ethyl-2-iso-pentyl-7,7,9,9-tetramethyl-1-oxa-4,8-diaza-spiro-[4.5]-decane
64. 2,2,7,7,9,9-Hexamethyl-1-oxa-4,8-diaza-3-oxo-8-acetyl-spiro-[4.5]-decane
65. 2,2-Diethyl-7,7,9,9-tetramethyl-1-oxa-4,8-diaza-3-oxo-8-acetyl-spiro-[4.5]-decane
66. 2,2,4,4-Tetramethyl-7-oxa-3,14-diaza-13-oxo-dispiro-[5.1.4.2]-tetradecane
67. 2,2,4,4-Tetramethyl-7-oxa-3,15-diaza-14-oxo-dispiro-[5.1.5.2]-pentadecane
68. 2,2,4,4-Tetramethyl-7-oxa-3,21-diaza-20-oxo-dispiro-[5.1.11.2]-heneicosane Suitable compounds of the formula (IVb) are the salts of the compounds of the formula (IVa) with protonic acids, for example hydrogen chloride, sulfuric acid, phosphoric acid and the like, for example the hydrochlorides of the above-indicated compounds No. 1-68. The following examples may be mentioned by way of illustration:

69. 2,2,7,7,9,9-Hexamethyl-1-oxa-3,8-diaza-4-oxo-spiro-[4.5-decane hydrochloride
70. 2,2,4,4-Tetramethyl-7-oxa-3,14-diaza-15-oxo-dispiro-[5.1.5.2]-pentadecane hydrochloride
71. 2,2,4,4-Tetramethyl-7-oxa-3,20-diaza-21-oxo-dispiro-[5.1.11.2]-heneicosane hydrochloride
72. 2,2,7,7,9,9-Hexamethyl-1-oxa-4,8-diaza-3-oxo-spiro-[4.5]-decane hydrochloride
73. 2,2-Diethyl-7,7,9,9-tetramethyl-1-oxa-4,8-diaza-3-oxo-spiro-[4.5]-decane hydrochloride
74. 2,2,4,4-Tetramethyl-7-oxa-3,14-diaza-13-oxo-dispiro-[5.1.4.2]-tetradecane hydrochloride
75. 2,2,4,4-Tetramethyl-7-oxa-3,15-diaza-14-oxo-dispiro-[5.1.5.2]-pentadecane hydrochloride
76. 2,2,4,4-Tetramethyl-7-oxa-3,21-diaza-20-oxo-dispiro-[5.1.11.2]-heneicosane hydrochloride Examples of the epoxides of the formula (V) are:

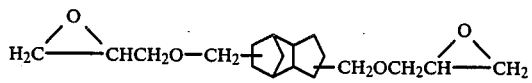

77.

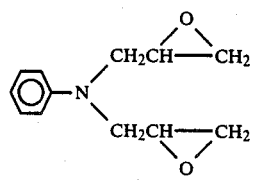

78.

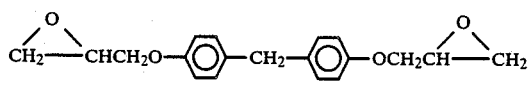

79.

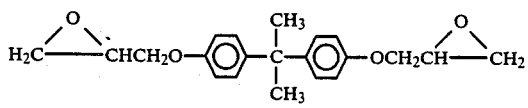

80.

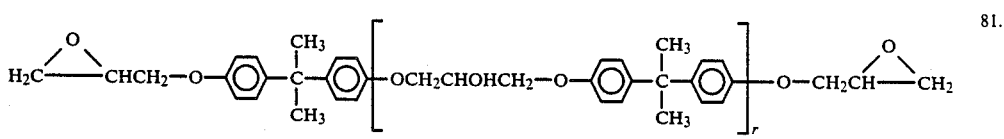

81.

with r = 1, 2, 3 . . .

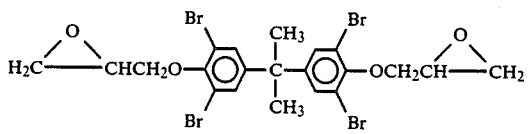

82.

-continued

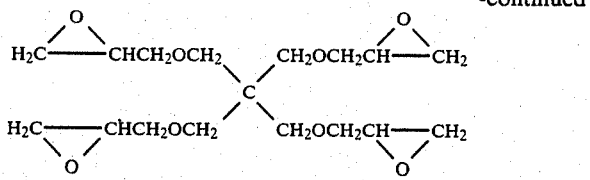
83.

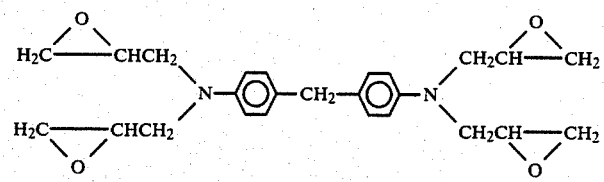
84.

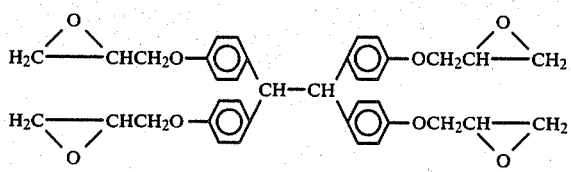
85.

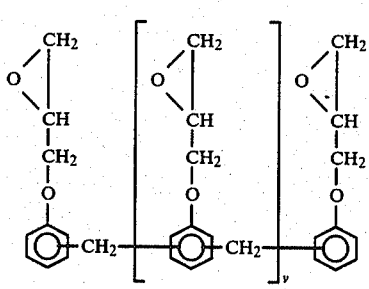

with v = 1, 2, 3 ...

86.

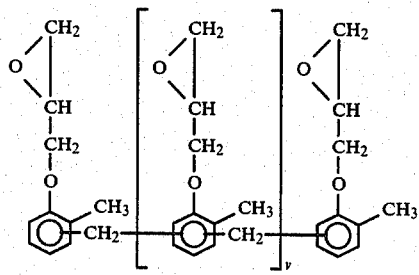

with v = 1, 2, 3 ...

87.

For the conversion to the stabilizers according to the invention, the compounds of the formula (V) need not be present in the pure form, but can also be used in the form of the corresponding epoxy resins of technical-grade quality.

The novel stabilizers can be incorporated in the polymers to be stabilized without problems, and are highly suitable for stabilizing the same against light-induced oxidative degradation, i.e. their being damaged through the action of oxygen, heat and light. In addition to the excellent stabilizer activity, the novel stabilizers are also distinguished by their good compatibility with the polymers to be stabilized.

Examples of polymers which can be stabilized successfully are:

Polymers which are derived from singly or doubly unsaturated hydrocarbons, for example polyolefins such as polyethylene, which may be crosslinked, polypropylene, polybut-1-ene, polyisobutene, polymethylbut-1-ene, polymethylpent-1-ene, polyisoprene, polybutadiene, polystyrene, copolymers of the monomers underlying the homopolymers mentioned, such as ethylene-propylene copolymers, propylene-but-1-ene copolymers, propylene-isobutene copolymers styrene-butadiene copolymers and also terpolymers of ethylene and propylene with a diene, such as, for example hexadiene, dicyclopentadiene or ethylidenenorbornene; mixtures of the abovementioned homopolymers, such as, for example mixtures of polypropylene and polyethylene, polypropylene and polybut-1-ene, polypropylene and polyisobutene or of butadiene-acrylonitrile copolymers with a styrene-butadiene copolymer.

Halogen-containing vinyl polymers, such as polyvinyl chloride, polyvinylidene chloride, polyvinyl fluoride, polychloroprene, chloro rubbers and also copolymers of vinyl chloride and vinylidene chloride with each other and with other olefinically unsaturated monomers.

Polymers which are derived from α,β-unsaturated acids and derivatives thereof, such as polyacrylates and polymethacrylates, polyacrylamides and polyacrylonitrile and also copolymers thereof with one another and with other vinyl compounds, such as acrylonitrile-butadiene-styrene, acrylonitrile-styrene and acrylonitrile-styrene-acrylate copolymers.

Polymers which are derived from unsaturated alcohols and amines and their acrylic derivatives or acetals, such as polyvinyl alcohol, polyvinyl acetate, stearate, benzoate, maleate, polyvinyl butyral, polyallyl phthalate, polyallylmelamine and copolymers thereof with other vinyl compounds, such as ethylene-vinyl compounds, such as ethylene/vinyl acetate copolymers. Homopolymers and copolymers which are derived from epoxides, such as polyethylene oxide, or the polymers which are derived from bisglycidyl ethers.

Polyacetals, such as polyoxymethylene and polyoxyethylene and also those polyoxymethylenes which contain ethylene oxide as a comonomer.

Polyurethanes and polyureas

Polycarbonate

Polyamides and copolyamides which are derived from diamines and dicarboxylic acids and/or from aminocarboxylic acids or the corresponding lactams, such as nylon 6, nylon 6/6, nylon 6/10, nylon 11, nylon 12.

Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate.

Crosslinked polymers which are derived from aldehydes on the one hand and phenols, ureas and melamines on the other, such as phenol-formaldehyde, urea-formaldehyde and melamine-formaldehyde resins.

The novel compounds can finally also be used as stabilizers in the resin and surface coatings sector. Examples are thermoset and themoplastic acrylic resins which are used for automotive coatings, acrylic resin finishes, i.e. the customary baking finishes and also very particularly mixtures based on hot-crosslinkable acrylic resin and styrene and also surface finishes and coatings based on acrylic-melamine resin and alkyd/acrylic/-melamine resin. Such surface coatings can contain as further additives other customary light stabilizers, phenolic antioxidants, pigments, dyes, metal deactivators, etc.

Of particular importance is the stabilization of polyolefins, styrene polymers, polyamides, poly(meth)acrylates and polyurethanes, for which the compounds are particularly suitable. Examples thereof are polyethylene of high and low density, polypropylene, ethylene-propylene copolymers, polystyrene, styrene-butadiene-acrylonitrile terpolymers, mixtures of polyolefins or of styrene polymers and also polyurethanes based on polyethers or polyesters.

The novel stabilizers are incorporated in the polymer compositions by generally customary methods. The incorporation can be effected for example by mixing the compounds and, if desired, further additives into the melt by the methods customary in the art, before or during shaping, or alternatively by applying the dissolved or dispersed compounds to the polymer directly or mixing into a solution, suspension or emulsion thereof, if desired with subsequent evaporation of the solvent. The amounts are 0.01 to 5, preferably 0.05 to 2.5 and in particular 0.1 to 10, % by weight, based on the material to be stabilized. The novel compounds can also be added to the plastics to be stabilized in the form of a master batch which contains these compounds, for example, in a concentration of 1 to 50, preferably 2.5 to 20, % by weight.

The plastics stabilized by the addition of the substances according to the invention can if desired also contain other known customary additives, such as, for example, antioxidants based on phenols or sulfides, metal deactivators and light stabilizers, phosphite stabilizers, metal compounds, epoxy stabilizers and polyhydric alcohols.

Examples of antioxidants are sterically hindered phenols such as 2,6-di-tert.-butyl-4-methylphenol, 4,4'-butylidene-bis-(2,6-di-tert.-butylphenol), 4,4-thio-bis-(2-tert.-butyl-5-methylphenol), 2,5-di-tert.-butyl-4-hydroxyanisole, dioctadecyl 2,2-bis-(3,5-di-tert.-butyl-2-hydroxybenzyl)-malonate, 1,3,5-tris-(3,5-di-tert.-butyl-4-hydroxybenzyl)-2,4,6-trimethylbenezene, 2,4,6-tri-(3,5-di-tert.-butyl-4-hydroxybenzyl)-phenol, phenolic triazine compound such as 1,3,5-tris-(3,5-di-tert.-butyl-4-hydroxybenzyl) isocyanurate, esters or amides of β-(3,5-di-tert.-butyl-4-hydroxyphenyl)-propionic acid with, for example, octadecanol, 1,6-hexanediol, 2,2'-thioethylene glycol, pentaerythritol and trishydroxyethyl isocyanurate, hexamethylenediamine, esters of 3,3-bis-(3-tert.-butyl-4-hydroxyphenyl)-butanoic acids with, for example, ethylene glycol, thiodipropionic acid esters with fatty alcohols, calcium or nickel salts of ethyl 3,5-di-tert.-butyl-4-hydroxybenzylphosphonate, dioctadecyl sulfide and disulfide.

Examples of metal deactivators are N,N'-diphenyloxamide, N-salicylal-N'-salicyloylhydrazine, N,N'-bis-salicyloylhydrazine, N,N'-bis-(3,5-di-tert.-butyl-4-hydroxyphenylpropionyl)-hydrazine, 3-salicyloylamino-1,2,4-triazole, bis-benzylideneoxalyl-dihydrazide, tris[2-tert.-butyl-4-thio(2'-methyl-4'-hydroxy-5'-tert.-butyl)phenyl-5-methylphenyl] phosphite, 2,2'-oxamido-bis[ethyl 3-(3,5-di-tert.-butyl-4-hydroxyphenyl)propionate].

The UV absorbers and light stabilizers include 2-(2'-hydroxyphenyl)-benzotriazoles such as, for example, the 5-chloro-3',5'-di-tert.-butyl and 5-chloro-3',5'-di-tert.-amylderivative, 2-hydroxybenzophenones such as, for example, the 4-heptoxy, 4-octoxy or 4-decyloxy derivative, salicylates such as octylphenyl salicylate, nickel complexes such as, for example the complex with 2,2'-thiobis-4-(1,1,3,3-tetramethylbutyl)-phenol and butylamine or other amines, or with 2-hydroxy-4-octoxybenzophenone, with dialkyldithiocarbamic acids or dialkyldithiophosphonic acids, oxamides and sterically hindered amines, for example bis(2,2,6,6-tetramethyl-4-piperidinyl) sebacate, polyesters of succinic acid with N-(2-hydroxyethyl)-2,2,6,6-tetramethyl-4-hydroxypiperidine, N,N'-bis(2,2,6,6-tetramethyl-4-piperidinyl)hexamethylenediamine, 2,2,4,4-tetramethyl-7-oxa-3,20-diaza-21-oxo-dispiro-[5.1.11.2]-heneicosane, 1,1'-(1,2-ethanediyl)bis-(3,3,5,5-tetramethylpiperzinone), condensation product of N,N'-bis-(2,2,6,6-tetramethyl-4-piperidyl)hexamethylenediamine with dibromoethane or with 4-tert.-octylamino-2,6-di-chloro-1,3,5-triazine or with 4-(N-morpholinyl)-2,6-di-chloro-1,3,5-triazine, tetrakis-(2,2,6,6-tetramethyl-4-piperidyl)-1,2,3,4-butanetetracarboxylic acid.

Suitable phosphites are aliphatic, aromatic or aliphatic-aromatic ones such as, for example, trisnonylphenyl phosphite, tris-(2,4-di-tert.-butylphenyl) phosphite, tris-(2-tert.-butylphenyl) phosphite or even esters of pentaerythritol phosphite.

Examples of metal compounds known for use as stabilizers are: calcium, barium, strontium, zinc, cadmium, magnesium, aluminum and lead soaps of aliphatic carboxylic acids or oxycarboxylic acids having about 12 to 32 carbon atoms, salts of said metals with aromatic carboxylic acids such as benzoates or salicylates and also (alkyl)phenolates of these metals, furthermore organotin compounds, such as, for example, dialkyltin thioglycolates and carboxylates, and also metal oxides, for example oxides of calcium, magnesium, zinc, aluminum or of silicon.

Known epoxy stabilizers are for example epoxidized higher fatty acids such as epoxidized soybean oil, tall oil, linseed oil or epoxidized butyl oleate and also epoxides of long-chain olefins and polyether epoxides.

Polyhydric alcohols can be for example pentaerythritol, trimethylolpropane, sorbitol or mannitol, i.e. preferably alcohols having 5 or 6 carbon atoms and 2 to 6 OH groups.

An effective stabilizer combination for poly-α-olefins, such as, for example, high, medium and low pressure polymers of $C_2$- to $C_4$-α-olefins, in particular polyethylene and polypropylene or of copolymers of such α-olefins, comprises, based on 100 parts by weight of polymer, for example 0.01 to 5 parts by weight of one of the compounds to be used according to the invention, 0.05 to 5 parts by weight of a phenolic stabilizer, if desired 0.01 to 5 parts by weight of a sulfur-containing costabilizer and also if desired 0.01 to 3 parts by weight of a basic or neutral metal soap, such as, for example calcium stearate or zinc stearate or of the corresponding oxides, if desired 0.01 to 5 parts by weight of a phosphite or phosphonite stabilizer and also if desired 0.01 to 5 parts by weight of a known UV stabilizer from the group of the alkoxyhydroxybenzophenones, 4-hydroxyphenylbenzotriazoles, benzylidenemalomononitrile esters or of so-called quenchers, such as, for example, nickel chelates. Other customary additives are for example plasticizers, lubricants, emulsifiers, fillers, such as, for example, chalk, talc, asbestos, pigments, optical brighteners, flame retardants and antistatic agents.

The plastics stabilized according to the invention can be used in a very wide variety of forms, for example as films, fibers, ribbons, profiles or as binders for paints, adhesives or putties.

The following examples serve to explain the invention further.

EXAMPLE 1

2,2-Bis-{[2-hydroxy-3-(2,2,4,4-tetramethyl-7-oxa-3,20-diaza-21-oxo-dispiro-[5.1.11.2]-heneicos-20-yl]-1-propoxy]-phen-4-yl}-propane A 1-liter stirred apparatus equipped with dropping funnel, reflux condenser, internal thermometer and stirrer was charged with 250 ml of toluene, followed by 72.8 g of 2,2,4,4-tetramethyl-7-oxa-3,20-diaza-21-oxo-dispiro-[5.1.11.2]-heneicosane (educt 1, compound No. 30), 1 g of benzyltriethylammonium chloride, 38.5 g of bisphenol-A diglycidyl ether (educt 2, compound No. 80) and 4 g of 50% strength sodium hydroxide solution. After the batch had been heated up to 90° C. a further 12 g of 50% strength sodium hydroxide solution were added dropwise, and the stirring was continued for 6 h. The mixture was extracted 3 times with 100 ml of water. The organic phase was dried with $Na_2SO_4$, and the toluene was distilled off. At about 180° C. the residue was dried in vacuo for ½ h. This gave 108.2 g of colorless product melt which, after cooling down, was ground. The amorphous product had a glass transition point of 91°–95° C., a softening point of 122° C. and a drip point of 134° C. The molecular weight was found to be 1,100 (calculated 1,068).

EXAMPLE 2

2,2-Bis-{[2-hydroxy-3-(2,2,4,4-tetramethyl-7-oxa-3,20-diaza-21-oxo-dispiro-[5.1.11.2]-heneicos-20-yl)-1-propoxy]-phen-4-yl}-propane 80.1 g of 2,2,4,4-tetramethyl-7-oxa-3,20-diaza-21-oxo-dispiro-[5.1.11.2]-heneicosane hydrochloride were reacted in accordance with the procedure of Example 1, the stated amount of sodium hydroxide solution being increased to 33 g of 50% strength sodium hydroxide solution. Yield 107.9 g of the same product as in Example 1.

EXAMPLE 3

2,2-Bis-{[2-hydroxy-3-(2,2,7,7,9,9-hexamethyl-1-oxa-4,8-diazo-3-oxo-spiro-[4.5]-decan-4-yl)-1-propoxy]-phen-4-yl}-propane A 1-liter stirred apparatus equipped with internal thermometer, dropping funnel and reflux condenser was charged with 250 ml of toluene, followed by 55.3 g of 2,2,7,7,9,9-hexamethyl-1-oxa-4,8-diaza-3-oxo-spiro-[4.5]-decane hydrochloride (compound No. 72), 2,2-bis[(2,3-epoxypropyl)-phen-4-yl]propane (compound No. 80) and 19.8 g of potassium hydroxide, and the batch was heated up to 90° C. and stirred at that temperature for 5 h. The batch was subsequently filtered, the toluene distilled off and the residue dried at 180° C. in vacuo for ½ h. This gave 83.5 g of almost colorless product melt which, after cooling down, was ground. The product had a softening point of 100° C. and a molecular weight of about 900.

EXAMPLES 4 TO 17

According to Examples 1 and 2 the following compounds were prepared:

| Example No. | Educt 1 Compound No. | (g) | Educt 2 Compound No. | (g) | Product (g) | Softening point (°C.) |
| --- | --- | --- | --- | --- | --- | --- |
| 4 | 30 | 72.8 | 79 | 35.0 | 100.2 | 116 |
| 5 | 30 | 72.8 | 77 | 42.0 | 107.6 | 99 |
| 6 | 30 | 72.8 | 84 | 28.0 | 102.6 | 154 |
| 7 | 30 | 72.8 | 86 | 38.0 | 95.5 | 148 |
| 8 | 29 | 56.0 | 80 | 38.5 | 80.3 | 115 |
| 9 | 29 | 56.0 | 79 | 35.0 | 65.0 | 118 |
| 10 | 70 | 31.7 | 80 | 19.3 | 46.3 | 115 |
| 11 | 43 | 24.0 | 80 | 19.3 | 40.2 | 90 |
| 12 | 43 | 24.0 | 77 | 21.0 | 40.0 | 68 |

-continued

| Example No. | Educt 1 Compound No. | (g) | Educt 2 Compound No. | (g) | Product (g) | Softening point (°C.) |
|---|---|---|---|---|---|---|
| 13 | 43 | 24.0 | 86 | 18.0 | 38.5 | 106 |
| 14 | 43 | 24.0 | 83 | 17.0 | 36.1 | 86 |
| 15 | 43 | 24.0 | 84 | 22.0 | 35.5 | 152 |
| 16 | 43 | 24.0 | 85 | 19.2 | 38.2 | 80 |
| 17 | 72 | 27.7 | 80 | 19.3 | 41.7 | 90 |

EXAMPLE 18

This example shows the volatility of the stabilizers of Examples 1 and 10 compared with stabilizers of German Pat. No. 2,606,026 and German Offenlegungsschrift No. 3,104,294.

The volatilities were determined in an apparatus for thermogravimertric analysis. Equal amounts (500 mg) of the compoaunds according to the invention and of the comparative substances were to this end heated up in a stream of nitrogen (1 liter/min) to 300° C. at a heating-up rate of 2 K/min and the loss of substance was measured in percent by weight.

| Stabilizer of example | Loss of substance in % by weight on reaching ...°C. | | | |
|---|---|---|---|---|
| | 220 | 260 | 300 | 10 min at 300 |
| 1 | 0 | 0.1 | 0.8 | 2.4 |
| 10 | 0 | 0.1 | 0.5 | 1.3 |
| Comparison A[1] | 0.4 | 0.7 | 2.5 | 6.0 |
| Comparison B[2] | 0.8 | 2.8 | 12.3 | 29.8 |

[1]Stabilizer of Example 11 of German Offenlegungsschrift 3,104,294
[2]Stabilizer of Example 31 of German Patent 2,606,026

EXAMPLE 19

A mixture comprising
100 parts by weight of polypropylene powder (MFI 230/5: 4 g/10 min, density at 23° C. 0.903 g/cm³)
0.1 part by weight of pentaerythrityl tetrakis-2-(3,5-di-tert.-butyl-4-hydroxyphenyl)-propionate
0.1 part by weight of calcium stearate and
0.3 part by weight of the stabilizer according to the invention under test
was homogenized in a laboratory high-speed mixer. This mixture was injection-molded at 240° C. in an SP 50 Windsor injection-molding machine into 60×60×1 mm sheets. These sheets were die-cut into T-shaped test specimens in accordance with DIN 53,383.

To determine the heat aging resistance, these tests specimens were suspended in a circulating air drying cabinet in a motor-driven frame with rotating trays and subjected, with a constant fresh air supply, to a temperature of 140° C.

The time when in some areas incipient local embrittlement occurred, characterized according to DIN No. 53,383 by the formation of discolored, cloudy, partly crumbling areas, was recorded.

The results are shown in the table below:

| Stabilizer of example | Incipient embrittlement after ... days |
|---|---|
| 1 | 54 |
| 10 | 49 |
| Comparison A | 41 |
| Comparison B | 29 |
| Comparison C[1] | 29 |

[1]without stabilizer under test

EXAMPLE 20

The sheets prepared as described in Example 19 were exposed to light without added filter in a accelerated light exposure table-top instrument "Suntest" Original Hanau Quarzlampen GmbH. The exposure times to pronounced cracking (visual assessment with a microscope) were found to be as follows:

| Stabilizer of example | Exposure time to the appearance of pronounced cracking |
|---|---|
| 1 | 505 |
| 10 | 505 |
| Comparison A | 370 |
| Comparison B | 473 |
| Comparison C | 183 |

EXAMPLES 21 TO 24

Example 21

The stabilized mixture prepared in the preceding example was processed on a laboratory film blow molding unit (screw diameter 30 mm, length 20 D) into blow-molded films of about 100 μm in thickness. These films were die-cut into test specimens in accordance wit DIN No. 53,455, shape 3, reduced on the scale of 1:3.

To determine the light stability, these samples were subjected in an arrangement in accordance with DIN No. 53,387 No. 5.1 note 2 in a ®Xenotest 1200 accelerated exposure and weathering instrument (Original Hanau Quarzlampen GmbH) to irradiation with alternating light. The radiation intensity was modulated by UV filters (special filter glass d=1.7 mm). The light stability was tested in accordance with DIN 53,387 (17 min dry period, 3 min spraying with water, black panel temperature 45° C., relative humidity during the dry period 70 to 75%). The parameter measured was the elongation at break on a tensile tester using a take-off speed of 5 cm/min after a certain exposure time.

The results have been tabulated in the table below.

| Stabilizer of example | Exposure time to 50% value (elongation at break relative to starting value) | 10% value |
|---|---|---|
| 1 | 300 h | 400 h |
| 10 | 360 h | 400 h |
| Comparison A | 220 h | 240 h |
| Comparison B | 280 h | 300 h |
| Comparison C | 130 h | 140 h |

EXAMPLE 22

Films and test specimens were prepared as described in Example 21 from the following mixture:
100 parts by weight of HD polyethylene powder (MFI 190/5 1.7 g/10 min, density 0.943 g/cm$^3$) and
0.15 part by weight of the stabilizer to be tested Exposure to light analogously to Example 21 in the Xenotest 1200 gave the following results:

| Stabilizer of example | Residual elongation at break relative to the starting value after 915 h of exposure |
| --- | --- |
| 1 | 72% |
| 10 | 83% |
| Comparison A | 35% |
| Comparison B | 53% |

EXAMPLE 23

The same measurement as in Example 22 was carried out on the following mixture:
100 parts by weight of HD polyethylene powder as described in Example 22 and
0.3 part by weight of the stabilizer to be tested

| Stabilizer of example | Residual elongation at break relative to the starting value after 1,194 h of exposure |
| --- | --- |
| 1 | 96% |
| 10 | 119% |
| Comparison A | 85% |
| Comparison B | 73% |
| Comoarison C | 8% |

EXAMPLE 24

According to Example 21 test specimens were prepared from the following mixture and exposed to light:
100 parts by weight of LD polyethylene powder (MFI 190/2.16 2.5 g/10 min; density 0.924 g/cm$^3$) and
0.3 part by weight of stabilizer to be tested The exposure results have been tabulated in the table below:

| Stabilizer of example | Exposure time to 50% value (residual elongation at break relative to the starting value) |
| --- | --- |
| 1 | 900 |
| Comparison A | 700 |
| Comparison B | 600 |
| Comparison C | 600 |

What is claimed is:

1. A compound of the formula (I)

$$\left[ \begin{array}{c} H_3C \\ R^1-N \\ H_3C \end{array} \begin{array}{c} CH_2R^2R^2 \\ \\ CH_2R^2 \end{array} \begin{array}{c} O \\ 1 \\ 5 \\ 4,3 \\ Y \\ | \\ CH_2CHCH_2-X \\ | \\ OZ \end{array} \begin{array}{c} R^3 \\ 2 \\ R^4 \end{array} R^5 \right]_n \quad (I)$$

in which n is a whole number from 1 to 20, $R^1$ is hydrogen, $C_1$- to $C_4$-alkyl, benzyl, allyl, $C_2$- to $C_{30}$-alkanoyl, $C_2$- to $C_{20}$-alkenoyl, $C_7$- to $C_{11}$-aroyl, $C_8$- to $C_{14}$-arylalkanoyl or $C_8$- to $C_{20}$-alkylaryl, $R^2$ is hydrogen or $C_1$- to $C_4$-alkyl, $R^3$ and $R^4$ are identical or different and denote hydrogen, $C_1$- to $C_{18}$-alkyl, phenyl which is unsubstituted or substituted by chlorine or $C_1$- to $C_4$-alkyl, $C_7$- to $C_{14}$-aralkyl which is unsubstituted or substituted by $C_1$- to $C_4$-alkyl, or together with the carbon atom connecting these radicals a $C_5$- to $C_{12}$-cycloalkyl or piperidine ring which is unsubstituted or substituted by up to four $C_1$- to $C_4$-alkyl groups, $R^5$ when n=1 denotes a piperidine ring which is substituted by 1 to 4 $C_1$- to $C_4$-alkyl groups, $R^5$ when n=2 denotes cycloalkylene, dicycloalkylene, tricycloalkylene, bismethylenemonocycloalkylene, bismethylenedicycloalkylene, bismethylenetricycloalkylene, arylene, bisarylenealkyl, which radicals can also be bromine- or chlorine- or $C_1$- to $C_4$-alkyl-substituted, a radical $$-R^6-O-[CH_2\underset{\underset{OZ}{|}}{C}HCH_2-O-R^6-O]_r$$

with r=1 to 20 and $R^6$=$C_2$- to $C_{12}$-alkylene, cycloalkylene, dicycloalkylene, tricycloalkylene, bismethylenemonocycloalkylene, bismethylenedicycloalkylene, bismethylenetricycloalkylene, arylene, bisarylenealkyl, which radicals can also be bromine- or chlorine- or $C_1$- to $C_4$-alkyl-substituted, $R^5$ when n=3 denotes the radical of a trifunctional alcohol or amine, the trifunctional radical of an aliphatic alcohol which contains further hydroxyl groups, the trifunctional radical of a novolak based on phenol, cresol, bisphenol-F or bisphenol-A, $R^5$ when n=4 denotes the tetrafunctional radical of an aliphatic alcohol or amine or of a novolak based on phenol, cresol, bisphenol-F or bisphenol-A or the radical $R^5$ when n>4 denotes a polyfunctional radical of a polyol, of a polyamine, of a novolak based on phenol, cresol, bisphenol-F or bisphenol-A, Y denotes $$\underset{O}{\overset{\diagdown 4 \quad 3 \diagup}{\underset{\|}{C}-N\diagdown}} \quad \text{or} \quad \underset{\diagup \atop O}{\overset{\diagdown 4 \quad 3 \diagup}{N-C\diagdown}}$$

and occupies ring positions 3, 4 in the formula (I),

X represents $-O-$ or $-\underset{\underset{R^7}{|}}{\overset{\|}{N}}-$, where $R^7$ is hydrogen, $C_1$- to $C_{30}$-alkyl, a piperidine ring which is substituted by 1 to 4 $C_1$- to $C_4$-alkyl groups, or a radical of the formula (II)

$$\begin{array}{c} H_3C\diagdown\phantom{N}\diagup CH_2R^2R^2 \\ R^1-N\phantom{xxx}\underset{5}{}\phantom{xxx}\underset{4,3}{}\overset{O}{\underset{1}{\diagup}}\overset{2}{\diagdown}\overset{R^3}{\diagdown}R^4 \\ H_3C\diagup\phantom{N}\diagdown CH_2R^2 \phantom{xxxx} \underset{|}{Y} \\ \phantom{xxxxxxxxxxxxxxxx} CH_2CHCH_2- \\ \phantom{xxxxxxxxxxxxxxxxxx} |\phantom{xxx} \\ \phantom{xxxxxxxxxxxxxxxxxx} OZ \end{array}$$ (II)

in which $R^1$, $R^2$, $R^3$, $R^4$ and Y have the above-mentioned meanings,

Z is hydrogen $R^5$ denotes in addition to the abovementioned meanings when n=1 hydrogen, $C_1$- to $C_{30}$-alkyl, aryl, aralkyl, alkylaryl or a piperidine ring which is substituted by 1 to 4 $C_1$- to $C_4$-alkyl groups and when n=2 $C_2$- to $C_{18}$-alkylene or phenylene, in which case X must then be equal to $-\underset{\underset{R^7}{|}}{N}-$, and the grouping $+N\!\!\!+_n R^5$
$\phantom{x}|$
$\phantom{x}R^7$ from the formula (I) stands
when n=2 for $-N\diagup\phantom{xx}\diagdown N-$
$\phantom{xx}\diagdown\underline{\phantom{xx}}\diagup$ and
when n>2 for a polyamine of the formulae $R^7-N+CH_2\!\!\!+_s N-R^7$, $R^7-N+CH_2\!\!\!+_s N+CH_2)_t N-R^7$ or
$\phantom{x}|\phantom{xxxxxxxxx}|\phantom{xxxxx}|\phantom{xxxxxxx}|\phantom{xxxxx}|$ $R^7-N+CH_2)_s N+CH_2\!\!\!+_t N+CH_2)_s N-R^7$,
$\phantom{x}|\phantom{xxxxxxx}|\phantom{xxxxxxx}|\phantom{xxxxxxx}|$ where $R^7$ has the abovementioned meaning and s and t are whole numbers from 2 to 4.

2. A compound as claimed in claim 1, wherein n is 2 to 5.

3. A compound as claimed in claim 2, wherein $R^2$ is hydrogen.

4. A compound as claimed in claim 1, wherein $R^2$ is hydrogen.

5. A process for preparing a compound of the formula I of claim 1, which comprises reacting a diazaspirodecane of the formula (IVa) or (IVb)

$$\begin{array}{c} H_3C\diagdown\phantom{N}\diagup CH_2R^2R^2 \\ R^1-N\phantom{xxx}\underset{5}{}\phantom{xxx}\underset{4,3}{}\overset{O}{\underset{1}{\diagup}}\overset{2}{\diagdown}\overset{R^3}{\diagdown}R^4 \\ H_3C\diagup\phantom{N}\diagdown CH_2R^2 \phantom{xxxx} \underset{|}{Y} \\ \phantom{xxxxxxxxxxxxxx} H \end{array}$$ (IVa)

$$\begin{array}{c} H_3C\diagdown\phantom{N}\diagup CH_2R^2R^2 \\ T.R^1-N\phantom{xx}\underset{5}{}\phantom{xxx}\underset{4,3}{}\overset{O}{\underset{1}{\diagup}}\overset{2}{\diagdown}\overset{R^3}{\diagdown}R^4 \\ H_3C\diagup\phantom{N}\diagdown CH_2R^2 \phantom{xxxx} \underset{|}{Y} \\ \phantom{xxxxxxxxxxxxxx} H \end{array}$$ (IVb)

in which $R^1$, $R^2$, $R^3$, $R^4$ and Y have the meanings specified in claim 1 and T is a nonoxidizing mineral acid or an aliphatic or aromatic sulfonic or phosphonic acid, an aliphatic mono-, di- or poly-carboxylic acid or an aromatic mono- or di-carboxylic acid, (A) with an epoxide of the formula (Va) or (Vb)

$R^5(-O-CH_2CH\overset{O}{\overline{\diagup\diagdown}}CH_2)_n$ (Va)

$R^5[-N(-CH_2CH\overset{O}{\overline{\diagup\diagdown}}CH_2)_2]_n$ (Vb)

(B) with epichlorohydrin as under (A) to give a compound of the formula (VI)

$$\begin{array}{c} H_3C\phantom{x}CH_2R^2R^2 \\ R^1-N\phantom{xxx}\underset{5}{}\phantom{xxx}\underset{4,3}{}\overset{O}{\underset{1}{\diagup}}\overset{2}{\diagdown}\overset{R^3}{\diagdown}R^4 \\ H_3C\phantom{x}CH_2R^2 \phantom{xxxx} \underset{|}{Y} \\ \phantom{xxxxxxxxxx} CH_2-CH\overline{\phantom{xx}}CH_2 \\ \phantom{xxxxxxxxxxxxxxx} \diagdown_O\diagup \end{array}$$ (VI)

and then reacting this compound with an alcohol of the formula (VII)

$R^5+OH)_n$ (VII)

or an amine of the formula (VIII)

$R^5+N-H)_n$
$\phantom{xx}|$
$\phantom{xx}R^7$ (VIII)

in which $R^1$, $R^2$, $R^3$, $R^4$, $R^5$, $R^7$, Y and n have the meanings specified in claim 1, or a polyamine of the formula (IX)

$R^7-N(-CH_2\!\!\!+_s\!\!\!+N(-CH_2\!\!\!+_u\!\!\!N(-CH_2\!\!\!+_s N-R^7$ (IX)
$\phantom{x}|\phantom{xxxxxx}|\phantom{xxxxxxx}|\phantom{xxxxxx}|$
$\phantom{x}H\phantom{xxxxxx}H\phantom{xxxxxxx}H\phantom{xxxxxx}H$ in which $R^7$, s and t have the abovementioned meanings and u is a whole number from 0 to 3.

6. A process as claimed in claim 5, wherein the reaction between a said diazaspirodecane with a said epoxide takes place in the presence of, in addition to the base, a phase transfer catalyst.

7. A process for stabilizing synthetic polymers comprising the step of adding to the polymers a compound as claimed in claim 1.

8. Process as claimed in claim 7, wherein the polymer is a polyolefin, a polyacrylate, a polymethacrylate or a homopolymer or copolymer of styrene.

9. Process as claimed in claim 7, wherein the polymer is the solids content of a paint.

10. A process for stabilizing synthetic polymers against the damaging influence of light, which comprises adding to the polymers, 0.01 to 5 parts by weight, based on a polymer, of a stabilizer as claimed in claim 1.

11. A process as claimed in claim 10, wherein said stabilizer is added in combination with conventional stabilizers.

12. A synthetic polymer stabilized against UV decomposition and containing 0.01 to 5 parts by weight, based on a polymer, of a stabilizer as claimed in claim 1.

* * * * *